(12) United States Patent
Abdel-Monem et al.

(10) Patent No.: US 7,247,328 B2
(45) Date of Patent: Jul. 24, 2007

(54) CHROMIUM (III) ALPHA AMINO ACID COMPLEXES

(75) Inventors: Mahmoud M. Abdel-Monem, Moscow, ID (US); Michael D. Anderson, Eden Prairie, MN (US)

(73) Assignee: Zinpro Corporation, Eden Prairie, MN (US)

( * ) Notice: Subject to any disclaimer, the term of this patent is extended or adjusted under 35 U.S.C. 154(b) by 1252 days.

(21) Appl. No.: 10/161,163

(22) Filed: May 31, 2002

(65) Prior Publication Data

US 2003/0228394 A1    Dec. 11, 2003

(51) Int. Cl.
    *A23L 1/304*      (2006.01)
    *C07F 11/00*      (2006.01)

(52) U.S. Cl. .......................................... 426/74; 556/63
(58) Field of Classification Search ................. 556/63; 426/74

See application file for complete search history.

(56) References Cited

U.S. PATENT DOCUMENTS

| | | |
|---|---|---|
| 2,810,754 A | 10/1957 | Chang |
| 2,849,468 A | 8/1958 | Cardinal |
| 2,915,540 A | 12/1959 | Chang |
| 3,084,189 A | 4/1963 | Chang |
| 3,168,541 A | 2/1965 | Hobbs |
| 3,174,986 A | 3/1965 | Shin-Ichi Motozaki |
| 3,463,858 A | 8/1969 | Anderson |
| 3,911,117 A | 10/1975 | Ender |
| 3,925,433 A | 12/1975 | Abdel-Monem |
| 3,941,818 A | 3/1976 | Abdel-Monem |
| 3,950,372 A | 4/1976 | Abdel-Monem |
| 4,021,569 A | 5/1977 | Abdel-Monem |
| 4,039,681 A | 8/1977 | Abdel-Monem |
| 4,067,994 A | 1/1978 | Anderson |
| 4,145,465 A | 3/1979 | Sanderson et al. |
| 4,167,564 A | 9/1979 | Jensen |
| 4,216,143 A | 8/1980 | Ashmead |
| 4,216,144 A | 8/1980 | Ashmead |
| 4,228,090 A | 10/1980 | Hydes |
| 4,425,280 A | 1/1984 | Ho |
| 4,460,734 A | 7/1984 | Owens et al. |
| 4,517,330 A | 5/1985 | Zdanowski et al. |
| 4,599,152 A | 7/1986 | Ashmead |
| 4,670,269 A | 6/1987 | Abdel-Monem |
| 4,678,854 A | 7/1987 | Abdel-Monem |
| 4,764,633 A | 8/1988 | Anderson |
| 4,830,716 A | 5/1989 | Ashmead |
| 4,900,561 A | 2/1990 | Abdel-Monem |
| 4,948,594 A | 8/1990 | Abdel-Monem |
| 4,956,188 A | 9/1990 | Anderson |
| 5,061,815 A | 10/1991 | Leu |
| 5,200,198 A | 4/1993 | Geisslinger et al. |
| 5,278,329 A | 1/1994 | Anderson |
| 5,401,770 A | 3/1995 | Taguchi et al. |
| 5,409,905 A | 4/1995 | Eby, III |
| 5,430,164 A | 7/1995 | Abdel-Monem |
| 5,504,055 A | 4/1996 | Hsu |
| 5,505,968 A | 4/1996 | Schaefer et al. |
| 5,516,925 A | 5/1996 | Pedersen et al. |
| 5,569,458 A | 10/1996 | Greenberg |
| 5,583,243 A | 12/1996 | Abdel-Monem |
| 5,698,724 A | 12/1997 | Anderson |
| 5,728,675 A | 3/1998 | Schaefer et al. |
| 5,885,610 A | 3/1999 | Anderson |
| 6,126,928 A | 10/2000 | Swaile |
| 6,166,071 A | 12/2000 | Ashmead et al. |
| 6,169,118 B1 | 1/2001 | Bilali |
| 6,210,690 B1 | 4/2001 | Nabeshima et al. |
| 6,218,192 B1 | 4/2001 | Altura et al. |
| 6,242,009 B1 | 6/2001 | Batarseh et al. |
| 6,248,368 B1 | 6/2001 | Valletta |
| 6,323,354 B1 | 11/2001 | Moore |
| 6,689,383 B1 | 2/2004 | Anderson et al. |

OTHER PUBLICATIONS

Morishita et al. "The Magnetic Susceptibilities of Mononuclear and Binuclear Chromium(III) Complexes" Bulletin of the Chemical Society of Japan 1965, vol. 38, Iss 8, pp. 1276-1279.*

* cited by examiner

*Primary Examiner*—Kamal A. Saeed
*Assistant Examiner*—Joseph R. Kosack
(74) *Attorney, Agent, or Firm*—McKee, Voorhees & Sease, P.L.C.

(57) ABSTRACT

Chromium (III) 1:3 complexes of alpha amino acids such as methionine are used as animal nutritional supplements. The chromium ion is complexed with three Methionine molecules to form the coordination complex anion $[CR(met)_3^+]$. The complex is easily absorbed to provide a bioavailable source for methionine, chromium and for nutritional supplementation of animals.

14 Claims, No Drawings

CHROMIUM (III) ALPHA AMINO ACID COMPLEXES

FIELD OF THE INVENTION

Bioavailable chromium complexes for use in animal nutrition.

BACKGROUND OF THE INVENTION

The essential role of chromium in nutrition was first recognized by Schwarz and Mertz in 1959 (Schwarz, K. and Mertz, W., "Chromium (III) and the glucose tolerance factor." *Archs Biochem. Biophys.* 85:292 (1959)). These researchers observed that rats fed torula yeast developed glucose intolerance. However, rats fed brewer's yeast did not develop this condition. A substance present in the brewer's yeast, but not in torula yeast was termed glucose tolerance factor (GTF). Later it was demonstrated that the active ingredient in GTF is chromium (III). Since these early observations, numerous avenues of research were initiated to better understand the nutritional role of chromium. Although much is now known about the role of chromium in human and animal nutrition, there is much that is not known and many of the effects of chromium in human disease are still controversial and not well documented. Recently, several reviews have been published that summarize the current state of knowledge regarding the role of chromium in nutrition. ("Chromium as a Supplement", Henry C. Lukaski, *Ann Rev Nutr.* 19:279(1999); "Chromium, Glucose Intolerance and Diabetes", Richard A. Anderson, *Journal of the American College of Nutrition*, 17, 548(1998); "The Biochemistry of Chromium", John B. Vincent, *J. Nutr.* 130: 715(2000); "Quest for the Molecular Mechanism of Chromium Action and its Relationship to Diabetes", John B. Vincent, *Nutrition Reviews*, 58: 67(2000))

The exact nature of the Glucose Tolerance Factor originally proposed in 1959 remains elusive. A chromium-containing material that potentiated glucose metabolism was partially purified from acid-hydrolyzed Brewer's yeast and porcine kidney. The material from yeast received the most attention and was commonly referred to as yeast GTF. It was reported that chromium in yeast GTF was absorbed more readily than inorganic chromium sources. Further, it was proposed that yeast GTF is composed of chromium (III) ions, nicotinic acid, glycine, glutamic acid and cysteine. ("Preparation of chromium-containing material of glucose tolerance factor activity from Brewer's yeast extracts and by synthesis, E. W. Toepfer", W. Mertz, M. M. Polansky et al., *J. Agric Food Chem*, 25:162(1977)) The proposed composition of the yeast GTF remains controversial and its isolation was not reproducible in other laboratories. Additionally, it has been proposed that the isolated yeast GTF may be an artifact produced by acid hydrolysis of special chromium binding proteins. ("Is glucose tolerance factor an artifact produced by acid hydrolysis of low-molecular-weight, chromium binding substance?" K. H. Sumrall and J. B. Vincent, *Polyhedron*, 16: 4171(1997)).

Recently, some progress was made towards understanding the molecular basis of the action of chromium in regulating carbohydrate and lipid metabolism. A peptide known as low-molecular-weight chromium-binding substance (LMWCr) has been isolated and is believed to play a critical role in modulating the action of insulin on its receptors. This peptide appears to be widely distributed in mammalian tissues and has been isolated from a number of sources. LMWCr is composed of glycine, cysteine, glutamic acid and aspartic acid. Glutamic and aspartic acids represent more than half the amino acid residues. The peptide is 1500 Dalton and binds four chromium ions. It is present in tissues primarily in its metal-free form. The amino acid sequence of this protein and the crystal structure of its complex with chromium are not yet known. ("The Biochemistry of Chromium", J. B. Vincent, *J. Nutr.* 130:715(2000)) It appears that LMWCr-bound chromium is present primarily in the form of anion bridged multinuclear chromium-carboxylate assembly. ("Synthetic Models for Low-Molecular-Weight Chromium-Binding Substance: Synthesis and characterization of Oxo-Bridged Tetranuclear Chromium (III) Assemblies", Truitt Ellis et al, *Inorg. Chem.*, 33: 5522(1994)) A synthetic multinuclear chromium assembly was found to activate the insulin receptor activity similar to that observed with the LMWCr. ("Synthetic Multinuclear Chromium Assembly Activates Insulin Receptor Kinase Activity: Functional Model for Low-Molecular-Weight Chromium-Binding Substance", C. M. Davis et al, *Inorg. Chem.*, 36:5316 (1997))

The recognition that yet an unidentified complex of chromium (III) and organic ligand(s) is responsible for modulating carbohydrate and lipid metabolism has generated significant interest in developing novel chromium containing compounds for use in human and animal nutrition. Numerous patents have been issued describing compounds that contain chromium bound to a variety of ligands. In 1975 a patent was issued to one of the inventors on this application disclosing 1:1 and 1:2 Chromium, Alpha Amino Acid Complex Salts (U.S. Pat. No. 3,925,433). These complex salts exist as ion pairs in which the cation is composed of a complex of the chromium (III) ion with one or two molecules of an alpha amino acid. The cation carries either a 1+ or a 2+ depending on the number of amino acid molecules forming the complex. The counter ion (anion) may be chloride, sulfate or acid sulfate. Essential metal complexes of L-methionine, including 1:1 chromium-L-methionine complexes are disclosed in U.S. Pat. No. 5,278,329. Metal complexes of amino acids obtained by hydrolysis of proteins, including chromium-amino acid complexes are described in U.S. Pat. No. 5,698,724.

A method for obtaining concentrated glucose tolerance factor from Brewer's yeast was described in U.S. Pat. No. 4,343,905 issued in 1982. Other patents were issued since describing methods for obtaining yeast or yeast derivatives possessing biological activities in modulating carbohydrate or lipid metabolism, e.g. U.S. Pat. Nos. 4,348,483; 6,140, 107; 6,159,466 and 6,248,323.

The use of the previously known compound, Chromium Acetylacetonate as a dietary supplement and pharmaceutical agent is described in U.S. Pat. No. 4,571,391. This water insoluble compound is heat stable, very stable to acids and slightly basic pH solutions. Chromium acetylacetonate is reported to be rapidly absorbed from the gastrointestinal tract after oral administration and is effective in potentiating insulin effects on glucose metabolism.

Dietary supplementation with essential metal picolinate, including chromium picolinate was first disclosed in U.S. Pat. No. 4,315,927 that was reissued on Jul. 7, 1992 as Re 33,988. In U.S. Pat. No. 4,315,927 the preparation of chromium picolinate was described (Example 4). In Re 33,988 specific claims are made to cover picolinate complexes of chromium, cobalt, copper and manganese in addition to zinc and ferrous that were covered in U.S. Pat. No. 4,315,927. A method for producing chromium picolinate complex is described in U.S. Pat. No. 5,677,461. The uses of chromium picolinate in the treatment and prevention of various diseases are disclosed in a number of patents including U.S. Pat. Nos. 5,087,623; 5,087,624; 5,175,156 and 6,329,361 B1. Compositions containing chromium picolinate and the uses of these compositions are described in U.S. Pat. Nos. 5,614,553; 5,929,066; 6,093,711; 6,136,317; 6,143,301; 6,251,888 B1 and 6,251,889 B1.

Chromium nicotinate, described as "GTF Chromium Material" and methods for its preparation were disclosed in U.S. Pat. Nos. 4,923,855 and 5,194,615. The use of chromium nicotinate for lowering blood lipid levels is described in U.S. Pat. No. 4,954,492. Compositions containing chromium nicotinate and their uses are disclosed in several patents including U.S. Pat. Nos. 5,905,075; 5,948,772; 5,980,905; 6,100,250; 6,100,251 and 6,323,192.

Pharmaceutical insulin-potentiating Cr (III) complexes possessing GTF-like activity are disclosed in U.S. Pat. No. 5,266,560. These complexes are composed of Cr (III), nicotinic acid or one of its derivatives and glutathione (a peptide containing L-glutamic acid, L-cysteine and glycine). The insulin potentiating activity of these complexes on glucose transport in isolated adipocytes in vitro is described and compared to that of similar complexes previously reported in the literature.

The use of metal proprionates, including chromium proprionate is disclosed in U.S. Pat. Nos. 5,707,679 and 6,303,158 B1. A composition containing chromium salts of short chain fatty acids and its use in animal nutrition is described in U.S. Pat. No. 5,846,581. Methods for producing metal carboxylate for use as animal feed supplements are described in U.S. Pat. Nos. 5,591,878 and 5,795,615.

Bioavailable chelates of creatine and essential metals, including chromium are described in U.S. Pat. No. 6,114,379. This patent claims a creatine-chromium complexes containing from 1-3 equivalents of the ligand for each chromium ion.

The use as a nutritional supplement or in the treatment of medical conditions of a previously known ti-nuclear chromium (III) complex is described in U.S. Pat. Nos. 6,149,948 and 6,197,816 B1. The complex is represented by the formula $[Cr_3O(O_2CCH_2CH_3)_6(H_2O)_3]^+$. The biological effects of the complex on a number of enzymes involved in carbohydrate and lipid metabolism are described in these patents. A method for the isolation of bovine low-molecular weight Cr-binding substance and its use are described in U.S. Pat. No. 5,872,102. This substance enhanced the insulin-activated uptake of glucose by rat adipocyts and activated rat adipocytic membrane tyrosine kinase and phosphotyrosine phosphatase activities.

Several shortcomings have been identified that limit the effectiveness of the various chromium complexes described in the literature. Chromium picolinate is the most popular of the commercially available chromium complexes. However this compound has limited water solubility and some recent studies questioned its safety. Although the lack of toxicity of chromium chloride and chromium picolinate has been demonstrated in rats ("Lack of Toxicity of Chromium Chloride and Chromium Picolinate in Rats", Anderson et al, *J. Amer. Coll. Nutr.* 16: 273(1997), recent studies reported that chromium picolinate cleaves DNA and produces chromosome damage in Chinese hamster ovary cells. ("The Nutritional Supplement Chromium (III) Tris (picolinate) Cleaves DNA", J. K. Speetjens et al, *Chem. Res. Toxicol.* 12:483 (1999) & "Chromium (III) picolinate produces chromosome damage in Chinese hamster ovary cells", D. M. Stearns, *FASEB J.,* 9:1643(1995)) A study of the in vivo distribution of chromium(III) picolinate in rats concluded that the short lifetime of this compound in vivo minimizes the potential toxic effects of this dietary supplement.("In Vivo Distribution of Chromium from Chromium Picolinate in Rats and Implications for the Safety of the Dietary Supplement", D. D. D. Hepburn and J. B. Vincent, *Chem. Res. Toxicol.,* 15:93(2002)). For these reasons, it is clear that an alternative source of dietary chromium that is soluble, bioavailable, efficacious and safe is needed.

It is a primary objective of this invention to fulfill the above described need.

It is another objective of this invention is to provide novel 1:3 complexes of chromium (III) and alpha amino acids for use as nutritional supplement for humans and domesticated animals.

A still further objective of the invention is to provide methods for preparation of these novel complexes.

Yet another objective is to provide and describe the desirable effects of these complexes on animal performance.

An another objective of the invention is to demonstrate the lack of toxicity of the novel complexes in laboratory animals.

The structures here are 1:3 complexes of chromium (III) and alpha amino acids. The structure and properties of most of the available nutritionally relevant chromium complexes have been previously studied. For example, the mononuclear and binuclear complexes of chromium (III) picolinate have been synthesized and their structures were determined by x-ray crystallography. The reaction of chromium (III) chloride with picolinic acid in water at a pH<4.0 produced the mononuclear complex in which the ratio of metal to amino acid is 1:3 (chromium tri-picolinate). However, if the pH of the solution was>4.0, the binuclear complex was formed. The ratio of chromium to amino acid in the binuclear complex is 1:2. ("Mononuclear and Binuclear Chromium (III) Picolinate Complexes", D. M. Stearns and W. H. Armstrong, *Inorg. Chem.,* 31:5178(1992)).

The composition and biological activity of chromium complexes of picolinic acid and nicotinic acid have also been studied. The chromium complexes formed with these pyridine carboxylic acids are different because of the differences in the structure of the two compounds. Nicotinic acid is not an alpha amino acid and hence serves as a mono-dentate ligand. It binds with chromium through the carboxylate anion and forms in and tri-nuclear complexes. Two complexes were formed between chromium and nicotinic acid, the 1:1 and 1:2. Neither complex had biological activity in the battery of tests used in this study except that the chromium dinicotinate potentiated insulin activity in rat isolated adipose tissue. Picolinic acid on the other hand is an alpha amino acid and serves as a di-dentate ligand. It binds with the chromium ion through the pyridine nitrogen and carboxyl oxygen to form a stable five-member ring. Three different complexes were obtained when a solution of chromium chloride was treated with picolinic acid depending on the ratio of picolinic acid to chromium in the reaction mixture. The addition of one or two molar equivalents of picolinic acid to the chromium chloride solution caused a change in the color of the solution. Adjusting the solution to pH 7.4 with sodium hydroxide resulted in the precipitation of the complexes. These complexes were found to be homogenous by High Performance Liquid Chromatography (HPLC). When one molar equivalent of picolinic acid was used the product had the structure Cr Pic $(H_2O)_2(OH)_2$. The precipitate obtained when two molar equivalents were used had the structure $Cr(Pic)_2(H_2O)(OH).(H_2O)$. Since these complexes were formed at pH>4 they are most likely the binuclear complexes. Neither of the two complexes had biological activity. The addition of three molar equivalents of picolinic acid to a solution of chromium chloride in water results in the formation of a red solid that precipitated from solution. This precipitate was found to be homogenous by HPLC. Analysis of the precipitate indicated that it is the chromium tri-picolinate monohydrate, Cr (Pic)$_3$.H$_2$O. This material is most likely the mononuclear complex. This complex increased glucose uptake by rat skeletal muscle cultures in vitro. Addition of the complex to rat diet produced significant decrease in plasma glucose and prevented glycation of hemoglobin. Dietary supplementation of the chromium tripicolinate in Humans resulted in a significant increase in lean body mass in both males and females. ("Composition and Biological Activity of Chromium-Pyridine Carboxylate complexes", G W Evans and D J Pouchnik, J. Inorg. Biochem., 49:177(1993))

It can therefore be seen that all of the structures currently available differ from the chromium compounds of the present invention which are a different empirical formula and a different stereochemistry.

SUMMARY OF THE INVENTION

This invention relates to the preparation of novel 1:3 chromium (III) complexes. These complexes contain chromium in the oxidation state plus 3. The chromium in the complex is bound with three molecules of an alpha amino acid. In contrast to known neutral chromium complexes that are practically insoluble in polar solvents, the novel complexes described in this patent are readily soluble in polar solvents such as water and methanol. The complexes are stable in acidic and basic solutions. These water-soluble complexes are useful sources of readily bioavailable chromium when added to diets. The use of these complexes as feed additives in animal nutrition improves animal performance. The complexes did not produce toxicity when fed to laboratory rats at high doses.

DETAILED DESCRIPTION OF A PREFERRED EMBODIMENT

Chromium exists in several oxidation states but the most stable and important state is Cr(III). In its most stable state, trivalent chromium has a coordination number of six (6). The hexacoordinated trivalent chromium forms octahedral complexes with a variety of ligands. These complexes are characterized by their relative kinetic inertness in aqueous solutions. The half-life of the ligand-displacement reaction of many of these complexes is several hours. Because of this kinetic inertness, many complexes can be isolated as solids and are stable in aqueous solution for relatively long times, even under conditions where they are thermodynamically unstable.

The present invention involves the design, synthesis and evaluation of novel safe and effective chromium-amino acid complexes. Features that impart biological activity to metal-amino acid complexes include water solubility, stability of the complex at the pHs of the GI contents, absorbability of the complex and the ability of the complex to participate in biochemical reactions. The safety of metal-amino acid complexes is enhanced by the use of natural amino acids and by improving its bioavailability to minimize the amount of metal added to the feed to meet the nutritional requirements of animals.

In U.S. Pat. No. 3,925,433 1:1 and 1:2 chromium-alpha amino acids complex salts are described. Although these complexes provide important nutritional advances over inorganic sources of chromium, they suffer from several shortcomings. Mixing a solution of chromium chloride with one, two or three molar equivalents of an alpha amino acid results in the formation of clear green solutions. The pHs of these solutions were 0.932, 1.324 and 1.627, respectively. Adjusting these solutions to pH 7 by the careful addition of sodium hydroxide or sodium carbonate solution resulted in the precipitation of chromium compounds indicating that these complexes may not be sufficiently stable at range of pH values that may be present in the gastrointestinal tract. When a solution of the chromium-alpha amino acid complex (1:3) was treated with three equivalents of sodium hydroxide, a purple precipitate was formed. This precipitate was practically insoluble in water, dilute acids and bases, methyl alcohol, ethyl alcohol, isopropyl alcohol and ethyl acetate. Elemental analysis and examination of its FTIR indicated that it is a mixture of the neutral complex of chromium-amino acid (1:3) together with some poly-nuclear chromium-amino acid complexes. The lack of solubility of this complex and its uncertain composition suggested that it is unlikely to be of nutritional value.

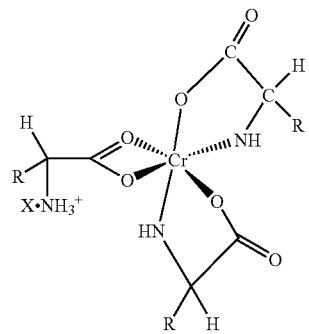

Structure 1

The novel complexes described in this invention are represented by structure 1 and are salts of the 1:3 chromium-amino acid complexes. These complexes exist as ion pairs in which the monovalent cation is composed of trivalent chromium complexed with three molecules of an alpha amino acid. One of the amino acid molecules retains its zwitterionic character to impart a net positive charge on the complex. The carboxylate group of this amino acid forms two bonds with the chromium (III) ion forming a strained four-member ring that satisfies two of the chromium six coordination sites. The other two alpha amino acid molecules bind to chromium through the alpha amino and carboxyl groups to form five member rings. This will satisfy all the six coordination bonds of chromium (III). The anion of the ion pair referred to here as "X" may be a monovalent anion such as chloride or a divalent anion such as sulfate. "R" is the organic moiety of an alpha amino acid. It can be derived from arginine, histidine, isoleucine, leucine, lysine, methionine, phenylalanine, threonine, tryptophan valine, glycine, etc. While glycine is not as an essential amino acid, it is also a preferred alpha amino acid in that it is readily available and can easily be utilized for synthesis of the complex salts of this invention. The two most preferred natural alpha amino acids are glycine and methionine. For glycine R represents hydrogen, and for methionine R represents the following: CH$_3$—SC—H$_2$—CH$_2$—.

These complexes can be prepared by using a simple and practical method. A solution of chromium chloride in water is heated to 90-95° C. The solution is usually dark green in color. The amino acid (3 molar equivalents) is carefully added and the heating is continued. The color of the solution slowly changes to dark blue-green. The solution is cooled to about 40° C. and sodium hydroxide solution is slowly and carefully added to adjust the solution to pH 3.9-4.0. Two molar equivalents of sodium hydroxide are required for the pH adjustment. The color of the solution turns to dark purple. Evaporation of the liquid provides a solid that is composed of the desired product and sodium chloride. The product can be separated from sodium chloride by extraction with methanol or ethanol. Alternatively, product may be separated from sodium chloride by chromatography on a suitable size exclusion resin.

The product obtained using the method described above has several unique properties. It exists as a stable solid. It is dark purple in color. The product is readily soluble in water and methanol, soluble in ethanol, sparingly soluble in isopropyl alcohol and insoluble in ethyl acetate. A 0.1 molar solution of the product in water has a pH of 4.078. The UV/Vis spectrum of the solution has absorption maxima at 400 nm (molar absorptivity, 44.08) and at 541 nm (molar absorptivity, 50.60). In contrast, the UV/Vis spectrum of chromium chloride has absorption maxima at 429 nm (molar absorptivity, 18.10) and at 608 nm (molar absorptivity, 14.43). The addition of as many as 20 molar equivalents of a 0.1 molar solution of sodium bicarbonate changed the pH of the solution to 8.097 but no precipitate was formed. In one experiment as much as 80 molar equivalents of the 0.1 molar solution of sodium bicarbonate was added. The pH of the mixture was 8.354 but no precipitate of chromium compounds were formed. In contrast, the addition of slightly more than 2 equivalents of 0.1 molar sodium bicarbonate to a 0.1M solution of chromium chloride resulted in the formation of a voluminous precipitate but the pH of the mixture was only 4.356. Adjusting the 0.1 molar solution of the complex to about pH 1.0 by the addition of 20 molar equivalents of hydrochloric acid did not decompose the complex as manifested by no change in the UV/is spectrum of the solution.

The solid complex obtained by using the method described above is homogenous by High Performance Liquid Chromatography. Analysis of a methanol solution by using a size exclusion column indicated the presence of a single component. Detection of the peak at two different wavelengths, one to detect chromium and the second to detect the amino acid indicated that both eluted in the single peak. Analysis of a methanol solution of chromium chloride indicated that it eluted as several peaks, none was similar to that of the complex. Further the major peak of chromium chloride had a shorter retention time than the complex indicating a larger molecular size.

Complexes with similar physico-chemical properties were obtained using different alpha amino acids. Elemental analysis of the complexes gave results consistent with the proposed structure. The FTIR spectrum of the complex is different than that of the amino acid used for forming the complex and is similar to that of amino acid complexes of other metals.

The complex formed between chromium (III) and L-methionine was tested as a nutritional source of chromium in dairy cows and was found to improve performance. Supplementing the diet with chromium tri-L-methionine hydrochloride did not affect the intake of dry matter in cows but increased milk production. The toxicity of the complex in rats was examined and found to be non-toxic in the doses used.

EXAMPLE 1

Preparation of Chromium (III) Tri-methionate Hydrochloride:

Water (550 ml) was placed in a 2000 ml-beaker. Chromium chloride hexahydrate (79.959 g, 0.3 moles) was added. The mixture was heated with stirring to boiling. L-Methionine (134.306 g, 0.9 moles) was added. The mixture was heated with stirring until the solids completely dissolved. Heating with stirring was continued for additional 30 minutes. The solution turned from dark green to dark blue-green. The solution was cooled to 30° C. Sodium hydroxide (23.316 g, 0.5829 moles) was dissolved in 100 ml water and the solution was cooled to 30° C. The sodium hydroxide solution was added dropwise to the chromium-methionine solution with stirring. The solution turned from dark blue-green to dark purple. The solution was evaporated to dryness under reduced pressure. The residue was extracted with methanol to leave a white crystalline solid. The methanol extract was evaporated to dryness to give a dark purple crystalline solid (161.352 g, yield 100.91%).

FTIR of product in a potassium Bromide pellet showed absorptions at: 3421.5(s), 2916.2(s), 1635.5(s), 1508.2(m), 1438.8(m), 1338.8(m), 1338.5(s), 1272.9(w), 1242.1(w) and 1145.6(m) cm$^{-1}$. (s=Strong, m=Medium, w=Weak)

The visible spectrum of a 0.01 M solution in water had two maxima at 400 nm (molar absorptivity, 44.08) and at 541 nm (molar absorptivity, 50.60).

The pH of a 0.1 molar solution in water was 4.078. A 10 ml portion was diluted with 200 ml of a 0.1 molar solution of sodium bicarbonate. No precipitate was formed. The solution had a pH of 8.097. An additional 600 ml of 0.1 molar sodium bicarbonate solution was added. No precipitate was formed and the pH of the solution was 8.354.

A solution of the complex in methanol containing the equivalent of 0.9555 mg/ml chromium was analyzed by HPLC on a 60A Macrosphere GPC column (Alltech Associates, Inc.) using methanol as mobile phase at a rate of 0.5 ml/min and a UV/Vis detector at 407 nm. A single peak with retention time of 6.48 min. was obtained. When a solution of chromium chloride hexahydrate containing the equivalent of 0.4666 mg/ml chromium was analyzed under the same condition a peak eluted with retention time of 6.67 min. The longer retention time indicates that the chromium complex has a larger molecular size than chromium chloride.

The HPLC analysis was repeated except for setting the detector to 210 nm to detect the amino acid. The sensitivity of detection was more than 100 folds greater than that at 405 nm and it was necessary to dilute the sample to contain 0.009555 mg/ml chromium. This diluted sample gave a single peak with retention time of 6.19 min at 407 nm. At 210 nm multiple minor peaks were observed with the major peak having retention time of 6.19 min. Analysis of a sample of L-methionine hydrochloride under the same condition with the detector set at 210 nm indicated the presence of several minor peaks in addition to the major peak at 7.6 min. These results indicate that the complex migrated on the column intact and that its molecular size is larger than that of chromium chloride and L-methionine hydrochloride.

EXAMPLE 2

Preparation of Chromium (III) Tri-leucinate Hydrochloride:

Water (150 ml) was placed in a 600 ml-beaker. Chromium chloride hexahydrate (13.325 g, 0.05 moles) was added. The mixture was heated with stirring to boiling. L-Leucine (19.685 g, 0.15 moles) was added. The mixture was heated with stirring until the solids completely dissolved. Heating with stirring was continued for additional 30 minutes. The solution turned from dark green to dark blue-green. The solution was cooled to 30° C. Sodium hydroxide (4.014 g, 0.10 moles) was dissolved in 20 ml water and the solution was cooled to 30° C. The sodium hydroxide solution was added dropwise to the chromium-leucine solution with stirring. The solution turned from dark blue-green to dark purple. The solution was evaporated to dryness under reduced pressure. The residue was extracted with methanol to leave a white crystalline solid. The methanol extract was evaporated to dryness to give a dark purple crystalline solid (28.363 g, Theory 23.948 yield 118.44% indicating that the product contains residual sodium chloride).

FTIR of product in a potassium Bromide pellet showed absorptions at: 3425.3(m), 2916.2(s), 1635.5(s), 1508.2(m), 1438.8(m), 1384.8.8(m), 1338.5(s), 1272.9(w), 1242.1(w) and 1141.8(m) $cm^{-1}$ (s=Strong, m=Medium, w=Weak)

The visible spectrum of a 0.01 M solution in water had two maxima at 406 nm (molar absorptivity, 38.79) and at 545 nm (molar absorptivity, 42.81).

The pH of a 0.1 molar solution in water was 3.996. A 10 ml portion was diluted with 200 ml of a 0.1 molar solution of sodium bicarbonate. No precipitate was formed. The solution had a pH of 7.987. The visible spectrum of the solution had two maxima at 409 m (molar absorptivity, 47.46) and at 558 nm (molar absorptivity, 47.67).

EXAMPLE 3

Preparation of Chromium Tri-methionate Hydrochloride Premix (0.1% Chromium):

A 100-ml of distilled water was measured into a 400-ml beaker. Chromium Chloride Hexahydrate (6.672 g, 0.0251 moles) was added and the mixture was heated with stirring until the solid was completely dissolved. L-Methionine (11.201 g, 0.0751 moles) was added and the mixture was heated with stirring. The color of the solution changed from dark green to blue-green. Heating at 90-95° C. was continued for additional 60 min. The solution was cooled to 30° C. A cooled solution of sodium hydroxide (1.967 g, 0.0492 moles) in 50 ml of water was added dropwise with stirring. The color of solution changed to dark purple. The solution was evaporated under reduced pressure. The residue was dissolved in 100 ml of methanol and the solution was added to 1000 g of a carrier. The mixture was placed in an oven at 60 ml for 24 hrs. A sample of the dried premix was analyzed as described in Example 1 by UV/Vis, colorimetry and HPLC. The premix was used in a feeding trial in swine.

EXAMPLE 4

Preparation of Chromium Trimethionate Solution (1.75% Chromium):

A 1500 ml of water was measured into a 4-1 beaker. Chromium Chloride Hexahydrate (390.993 g, 1.4675 moles) was added and was heated with stirring until the solids completely dissolved. Heating with stirring was continued for additional 1 hr to completely hydrate the chromium salt. L-methionine (1094.845 g, 7.338 moles) was added and the mixture was heated with stirring until all the solids dissolved. Heating with stirring was continued for 1 hr. The color of the solution changed to dark purple. The solution was completed to 4 liters with distilled water.

The pH of the solution was 2.336. It contained 25.61% methionine and 1.86% chromium.

The visible spectrum of a 0.01 M solution in water had two maxima at 416 nm (molar absorptivity, 102.5) and at 579.5 nm (molar absorptivity, 101.9).

The pH of a 0.1 molar solution in water was 2.285. A 10 ml portion was diluted with 200 ml of a 0.1 molar solution of sodium bicarbonate. No precipitate was formed. The solution had a pH of 7.546. The visible spectrum of the solution had two maxima at 409.5 nm (molar absorptivity, 43.89) and at 558 nm (molar absorptivity, 46.83).

EXAMPLE 5

Effects of Chromium Tri-L-Methionate Hydrochloride on Performance of Dairy Cows:

The effects of supplementation with chromium in the form of chromium tri-L-methionine hydrochloride on performance of periparturient dairy cows were studied. Seventy-two cows were used to determine whether milk production and dry matter intake were affected by chromium tri-L-methionine hydrochloride supplementation of the diet during the periparturient period. Cows were fed either a diet high in nonforage fiber sources or high in non-fiber carbohydrates from day 21 before expected parturition until parturition and then fed a common lactating diet. Chromium tri-L-methionine hydrochloride was supplemented once daily via gelcap at doses of 0, 0.03, or 0.06 mg Cr/kg of metabolic body weight. Chromium supplementation began on day 21 before expected parturition and continued until day 28 postpartum. Cows were milked after calving according to established procedures. Feed intake was recorded daily for each cow throughout the experiment. Samples of the diet were obtained weekly and the dry matter contents were determined. Individual milk weights were recorded at each milking during the lactating phase of the experiment. Milk samples were taken from all milkings during one 24-hours period each week, composited based on the amount of milk produced at each milking, and analyzed for fat, protein, lactose, and total solids.

Supplementing diets with chromium tri-L-methionine hydrochloride did not affect dry matter intake in cows. However, chromium supplementation tended to increase milk yield (P<0.13,Table 1).

TABLE 1

|  | Chromium tri-L-Methionine HCl mg/kg $BW^{.75}$ | | |
| --- | --- | --- | --- |
|  | 0.00 | 0.03 | 0.06 |
| Prepartum Dry Matter Intake kg/day | 13.6 | 13.9 | 13.7 |
| Postpartum Dry Matter Intake kg/day | 17.9 | 18.9 | 19.4 |
| Milk Production kg/day | 40.4 | 40.6 | 42.8 |
| Milk Fat kg/day | 1.73 | 1.76 | 1.81 |
| % Milk Fat | 4.43 | 4.41 | 4.33 |
| Milk Protein kg/day | 1.28 | 1.33 | 1.31 |
| % Milk Protein | 3.32 | 3.37 | 3.15 |
| Milk Lactose kg/day | 1.86 | 1.91 | 1.98 |
| % Milk Lactose | 4.63 | 4.69 | 4.61 |
| Milk Solids kg/day | 5.27 | 5.37 | 5.51 |
| % Milk Solids | 13.38 | 13.39 | 13.03 |

The chromium (III) complexes of this example and the invention can be used with conventional inert nutritional carriers such as distillers fermentation solubles, feed grains, poultry and fish bi-products, meal, whey, natural salt, ground corn cobs, feathermeal, etc.

EXAMPLE 6

Toxicity of Chromium Tri-L-Methionine Hydrochloride in Rat:

The toxicity of Chromium-L-Methionine Hydrochloride was studied in the rat following the administration of a single oral dose. Fifty 6 weeks old rats were used in the study (25 females and 25 males). Their body weight ranged from 130 to 220 g for males and 120-190 g for females. The animals were housed in polycarbonate cages over dust-free sawdust bedding in groups of five. The cages were placed in an air-conditioned room at 22° C. and 55% relative humidity. Rats were fed pelleted complete diet ad libitum. Animals were fasted overnight before dosing and given food 3-4 hours after dosing. Animals given water ad libitum. Animals were assigned at random to one of five treatments. Two groups of five animals each, one group of males and one group of females were assigned to each treatment. The treatments were control, 250 mg/kg, 500 mg/kg, 1000 mg/kg and 2000 mg/kg doses. A solution of the compound in water was administered in a single oral dose by gastric gavage. Animals were maintained for a 14-day observation period after receiving the dose. Surviving animals were killed on day 14. The weight of animals were recorded immediately before treatment, twice weekly for the study period and at death.

No animals died during the study and no treatment-related clinical signs were seen in the animals given the compound at any of the dose levels. Furthermore there were no macroscopic abnormalities in animals necropsied on day 14 after the oral dose. However, a 5% decrease in body weight gain was observed in male rats given the 2000 mg/kg dose. This dose is 4000 fold the recommended dose for pigs. Also, a dose related decrease in food consumption compared to control was noted in groups treated with the 1000 and 2000 mg/kg doses.

These results indicate that under these experimental conditions, the administration of a single oral dose of chromium tri-methionine in rat did not induce any toxicity at dose levels 1000 folds the recommended dose in pigs. The administration of a dose 2000 folds the recommended dose was associated with a decrease in food consumption, but was not associated with a decrease in the gain in body weight. At the 2000 mg/kg dose, which is 4000 folds the recommended dose; the decrease in food consumption was associated with a slight decrease in body weight gain.

What is claimed is:

1. A chromium complex of the formula:

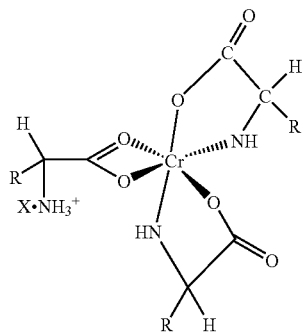

Structure 1 wherein "R" is an organic moiety normally present in a natural amino acid and "X" is a water soluble anion.

2. The complex of claim 1 wherein "X" is monovalent.

3. The complex of claim 1 wherein "X" is selected from the group consisting of chloride, bromide, iodide, sulphate, phosphate, acetate and propionate.

4. The complex of claim 1 wherein "R" is selected so that the natural amino acid is one selected from the group consisting of arginine, histidine, isoleucine, leucine, lysine, methionine, phenylalanine, threonine, tryptophan, valine and glycine.

5. A nutritional composition of enhanced bioavailability for livestock, comprising a chromium complex of the formula:

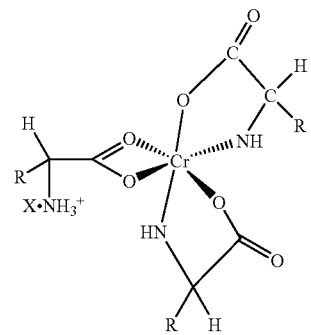

Structure 1 in combination with an animal nutrition carrier.

6. The complex of claim 5 wherein "X" is monovalent.

7. The complex of claim 5 wherein "X" is selected from the group consisting of chloride, bromide, iodide, sulphate, phosphate, acetate and propionate.

8. The complex of claim 5 wherein "R" is selected so that the natural amino acid is one selected from the group consisting of arginine, histidine, isoleucine, leucine, lysine, methionine, phenylalanine, threonine, tryptophan, valine and glycine.

9. The composition of claim 5 wherein the carrier is selected from the inert animal nutrition carrier group of natural salt, ground corn cobs, corn meal, and feathermeal.

10. A nutritional composition of enhanced bioavailability for livestock, comprising a chromium complex of the formula:

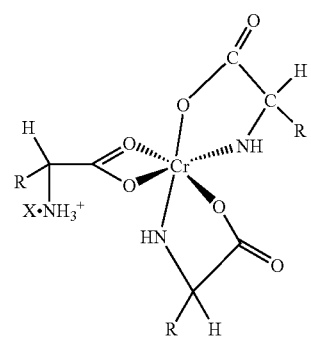

Structure 1 wherein "R" is an organic moiety normally present in a natural amino acid and "X" is a water soluble anion, all in a liquid form carrier.

11. The complex of claim 10 wherein "X" is monovalent.

12. The complex of claim 10 wherein "X" is selected from the group consisting of chloride, bromide, iodide, sulfate, phosphate, acetate and propionate.

13. The complex of claim 10 wherein "R" is selected so that the natural amino acid is one selected from the group consisting of arginine, histidine, isoleucine, leucine, lysine, methionine, phenylalanine, threonine, tryptophan, valine and glycine.

14. The composition of claim 10 wherein the solvent is selected from water, ethanol, molasses or any other suitable solvent or mixture of suitable solvents.

* * * * *